(12) United States Patent
Shen et al.

(10) Patent No.: US 8,342,323 B2
(45) Date of Patent: Jan. 1, 2013

(54) WATERPROOF HOUSING STRUCTURE FOR PORTABLE OPTICAL ANALYZER

(75) Inventors: Yen-Shih Shen, Taipei (TW); Shiarng-Bin Your, Taipei (TW); Ta-Chuan Weng, Taipei (TW)

(73) Assignee: Metertech Inc., Taipei (TW)

( * ) Notice: Subject to any disclaimer, the term of this patent is extended or adjusted under 35 U.S.C. 154(b) by 572 days.

(21) Appl. No.: 12/648,698

(22) Filed: Dec. 29, 2009

(65) Prior Publication Data

US 2011/0156548 A1 Jun. 30, 2011

(51) Int. Cl.
*B65D 85/38* (2006.01)
(52) U.S. Cl. .................................. 206/305; 206/320
(58) Field of Classification Search .............. 206/305, 206/320, 811, 701, 776, 722, 723; 455/90.3, 455/550.1, 575.1, 575.8; 356/244, 246
See application file for complete search history.

(56) References Cited

U.S. PATENT DOCUMENTS

| | | | | |
|---|---|---|---|---|
| 6,068,119 A * | 5/2000 | Derr et al. | ............ | 206/305 |
| 6,634,494 B1 * | 10/2003 | Derr et al. | ............ | 206/305 |
| 6,659,274 B2 * | 12/2003 | Enners | ............ | 206/305 |
| 6,995,976 B2 * | 2/2006 | Richardson | ............ | 206/320 |
| 7,333,194 B2 | 2/2008 | Jaunakais et al. | | |
| 7,436,653 B2 * | 10/2008 | Yang et al. | ............ | 361/679.01 |
| 7,775,354 B2 * | 8/2010 | Latchford et al. | ............ | 206/320 |
| 8,068,331 B2 * | 11/2011 | Sauers et al. | ............ | 206/305 |

* cited by examiner

*Primary Examiner* — Luan K Bui
*Assistant Examiner* — Chun Cheung
(74) *Attorney, Agent, or Firm* — Muncy, Geissler, Olds & Lowe, PLLC

(57) ABSTRACT

A waterproof housing structure for portable optical analyzer mainly comprises a hard upper casing, a lower casing and a fastening element. The hard upper casing contains an outer rim and an inner rim. The lower casing contains a hard inner shell and a pliable cap. The hard inner shell has a trapezoidal rim which has a first trapezoidal surface and a second trapezoidal surface lower than the first trapezoidal surface. The pliable cap wraps a portion of outer surface of the hard inner shell, and has an outer edge and an inner edge mating the upper casing. The fastening element fastens the hard upper casing to the lower casing. Thus the two irregular rims and edges can be coupled to prevent liquid permeation. Fabrication and assembly during production or repair and maintenance are simpler. It also improves grasp feeling and anti-slipping effect on the handgrip of the portable optical analyzer.

10 Claims, 6 Drawing Sheets

WATERPROOF HOUSING STRUCTURE FOR PORTABLE OPTICAL ANALYZER

FIELD OF THE INVENTION

The present invention relates to a housing of portable detectors and particularly to a waterproof housing structure for portable optical analyzer aiming to test liquid.

BACKGROUND OF THE INVENTION

Analyzers to test liquid for specific ingredient concentration such as liquid hardness, oxygen dissolution, residual chlorine, suspended matter and the like are widely used. For instance, U.S. Pat. No. 7,333,194 B2 provides a portable photometric analysis which has a detachable housing with a lengthy seam to facilitate repair and maintenance. An extra waterproof element (such as a rubber pad) has to be provided and coupled to prevent liquid from permeating into the housing. This makes fabrication and assembly complicated and difficult during production or maintenance. Moreover, the handgrip of the housing does not provide pliable touch and give users undesirable grasp feeling when in use. Its hard and smooth surface even easily causes the instrument slipping from user's hand and results in dropping and damage of the portable photometric analysis.

SUMMARY OF THE INVENTION

Therefore, the primary object of the present invention is to overcome the disadvantages of the conventional techniques to couple two irregular rims and prevent water permeation and improve usability.

Another object of the present invention is to make assembly simpler to facilitate production or repair and maintenance, and also improve grasp feeling and anti-slipping effect of the handgrip of portable optical analyzer.

To achieve the foregoing objects, the present invention provides a waterproof housing structure for portable optical analyzer that mainly comprises a hard upper casing, a lower casing and a fastening element. The hard upper casing includes an outer rim and an inner rim, an indented liquid sample chamber located on the surface and an upper fastening strut extended inside. The lower casing includes a hard inner shell and a pliable cap. The hard inner shell has a trapezoidal rim which has a first trapezoidal surface on an outer side and a second trapezoidal surface on an inner side lower than the first trapezoidal surface to mate and couple with the inner rim of the upper casing. The pliable cap wraps a portion of outer surface of the hard inner shell, and has an outer edge mating and coupling with the outer rim of the upper casing, and an inner edge mating with the interval of the outer rim and inner rim of the upper casing. The inner edge has a portion located on the first trapezoidal surface. The lower casing has an extended lower fastening strut corresponding to the upper fastening strut. The fastening element runs through the upper fastening strut to engage with the lower fastening strut to fasten the hard upper casing to the lower casing.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENT

Figure 1:
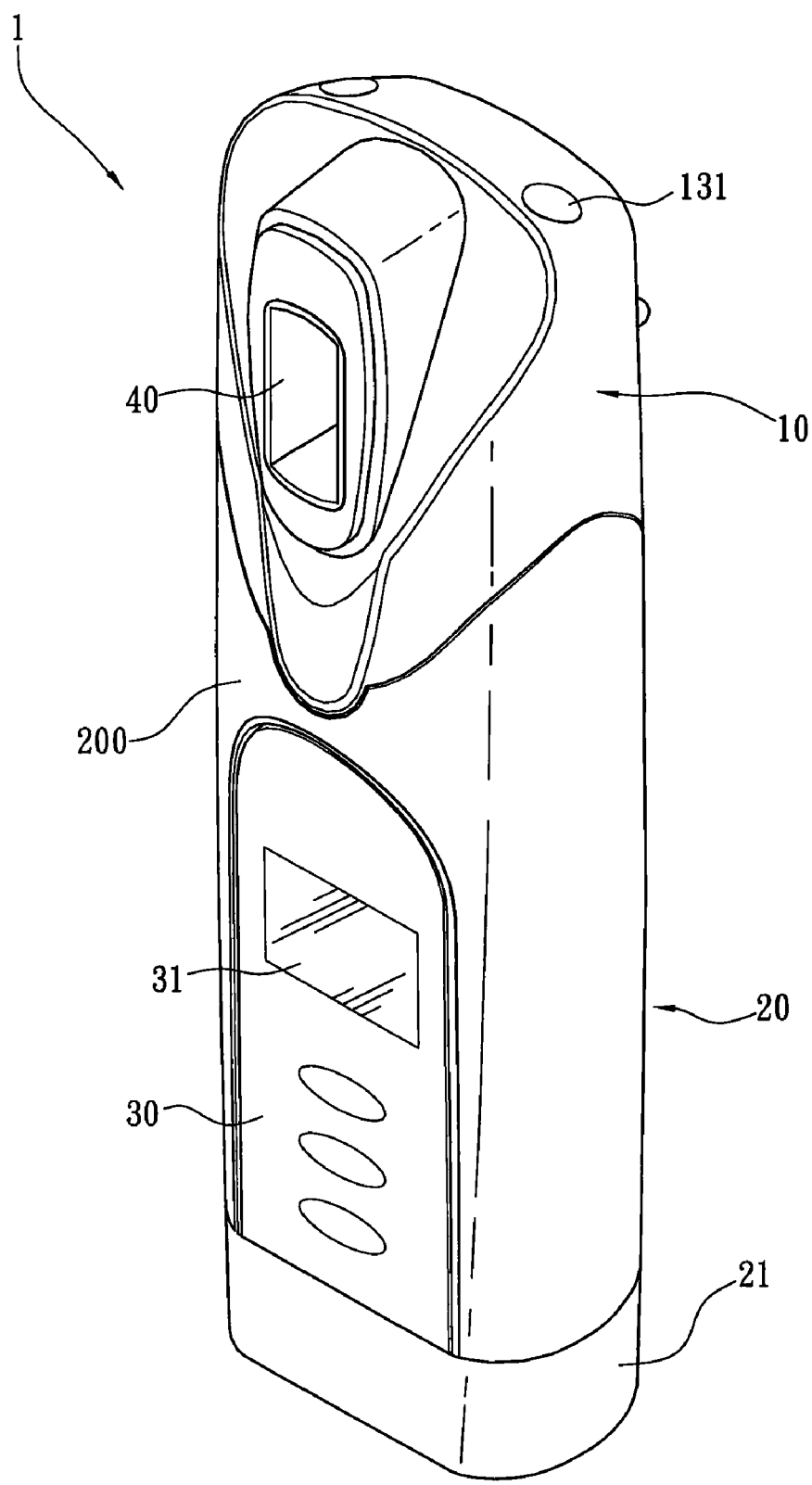
FIG. 1 is a perspective view of the present invention.
Figure 2:
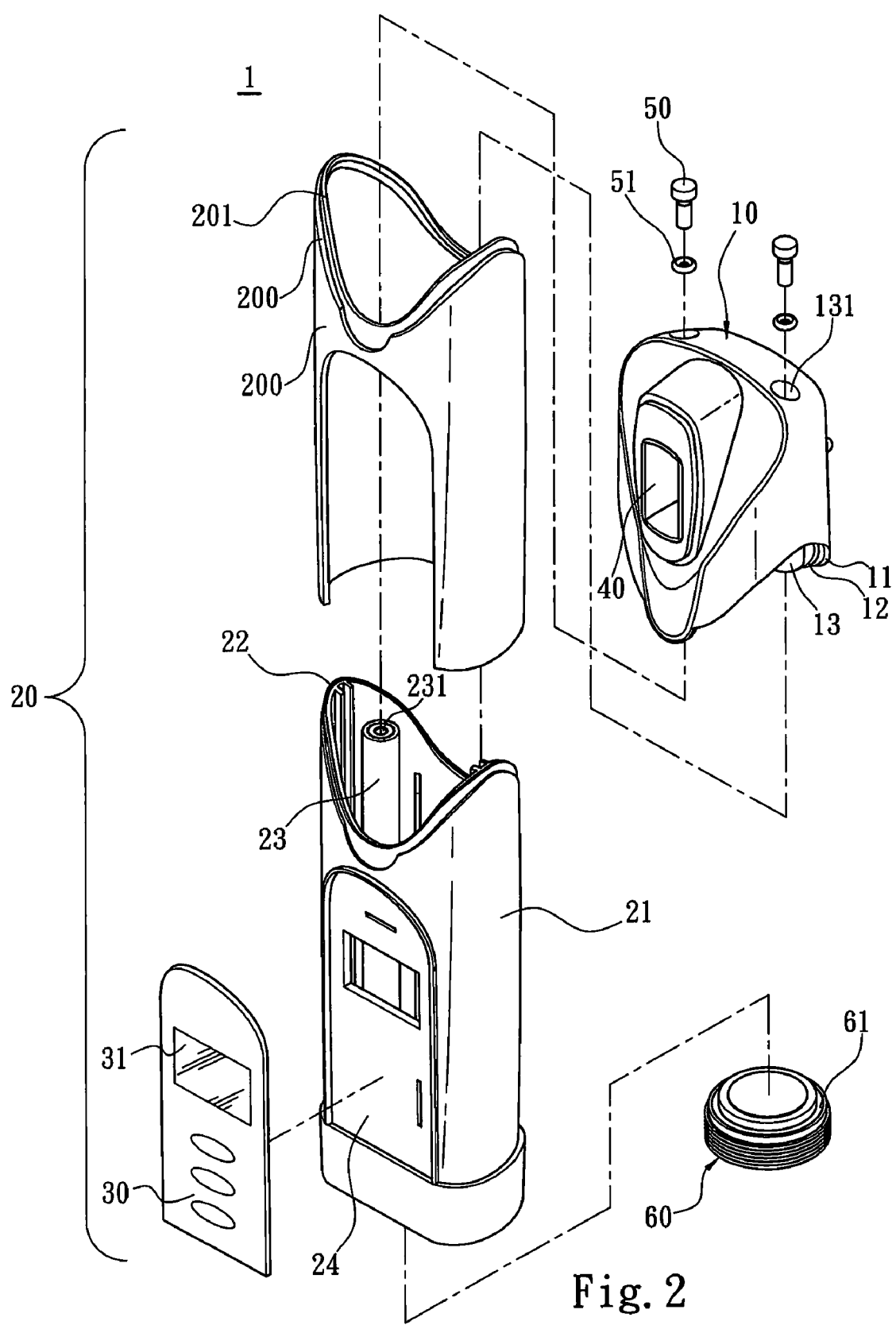
FIG. 2 is an exploded view of the present invention according to FIG. 1.
Figure 3A:
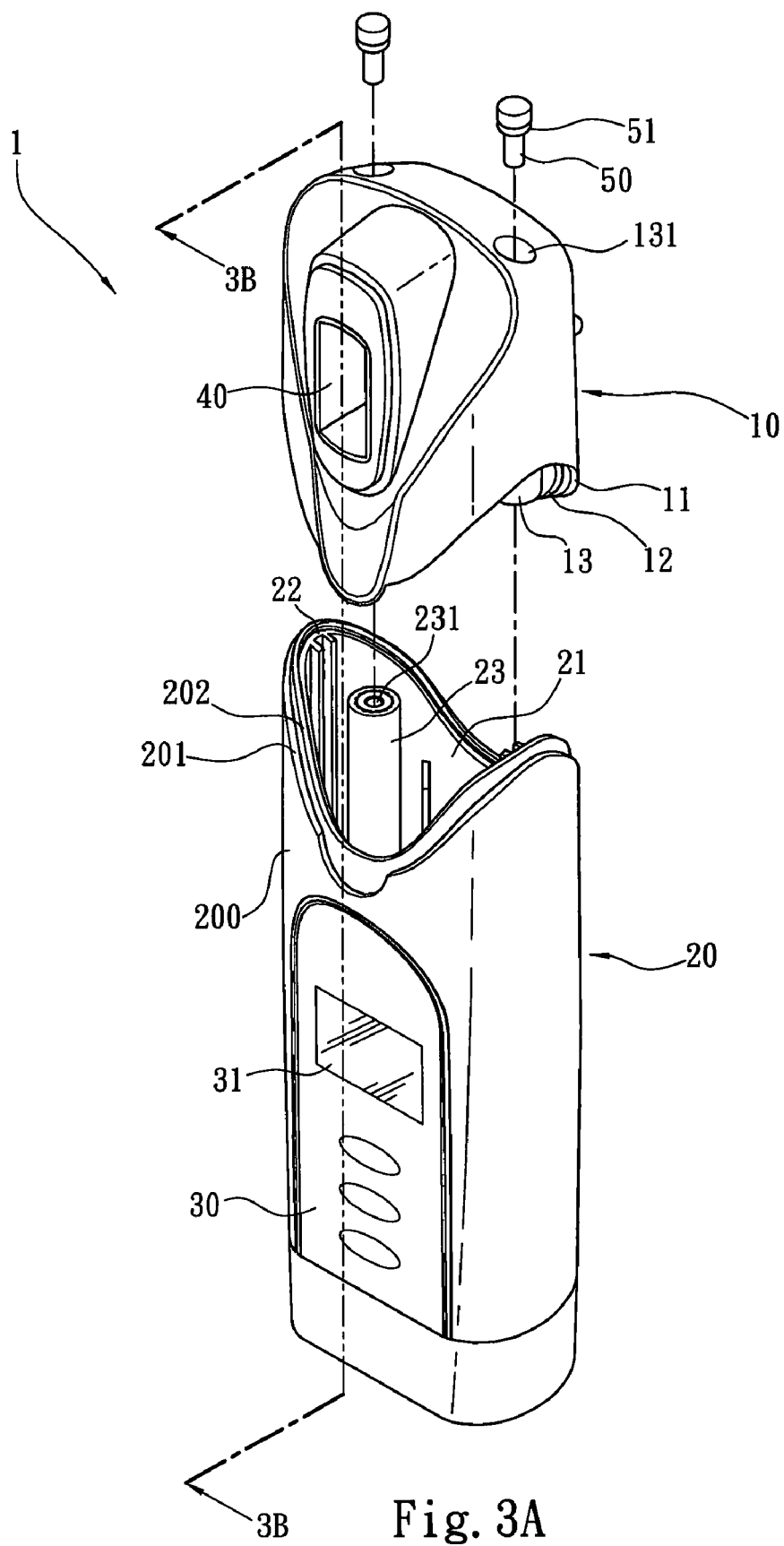
FIG. 3A is a fragmentary exploded view of the present invention according to FIG. 1.
Figure 3B:
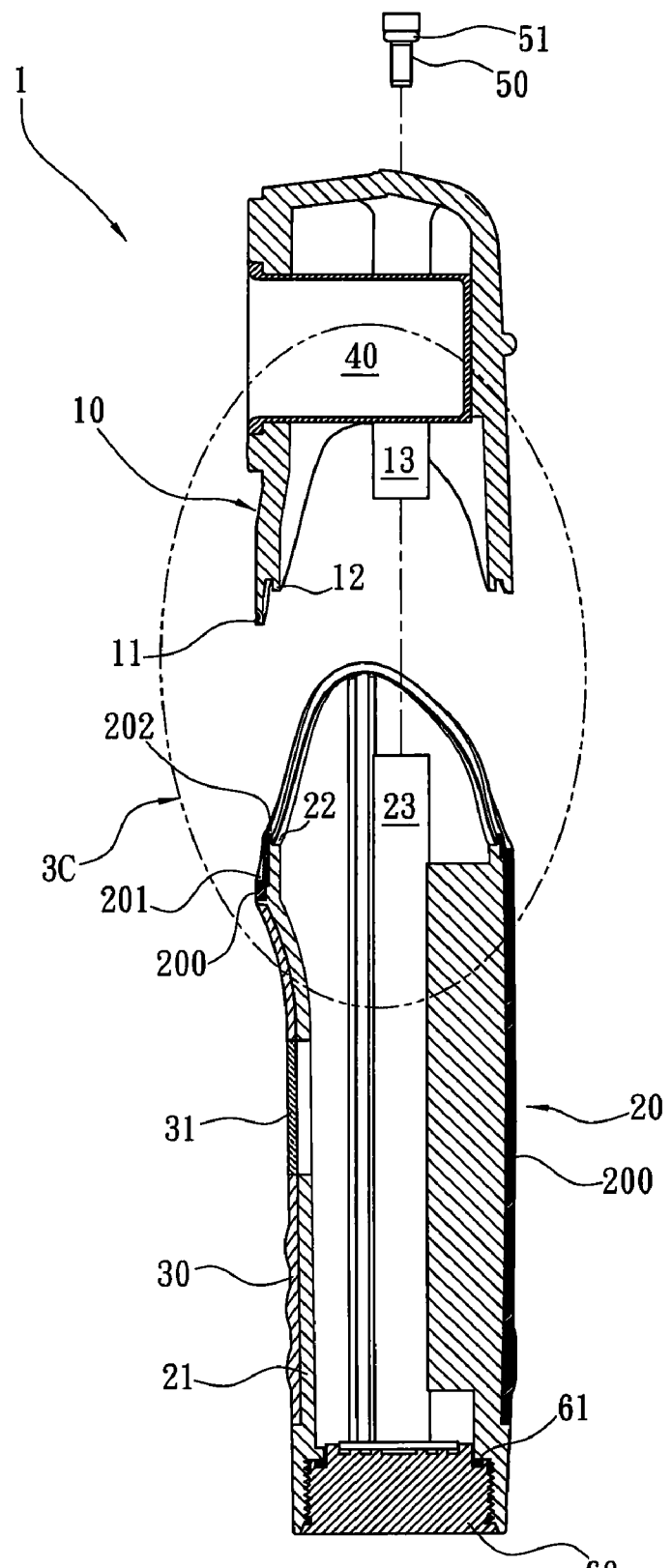
FIG. 3B is a sectional view taken on line 3B-3B in FIG. 3A.
Figure 3C:
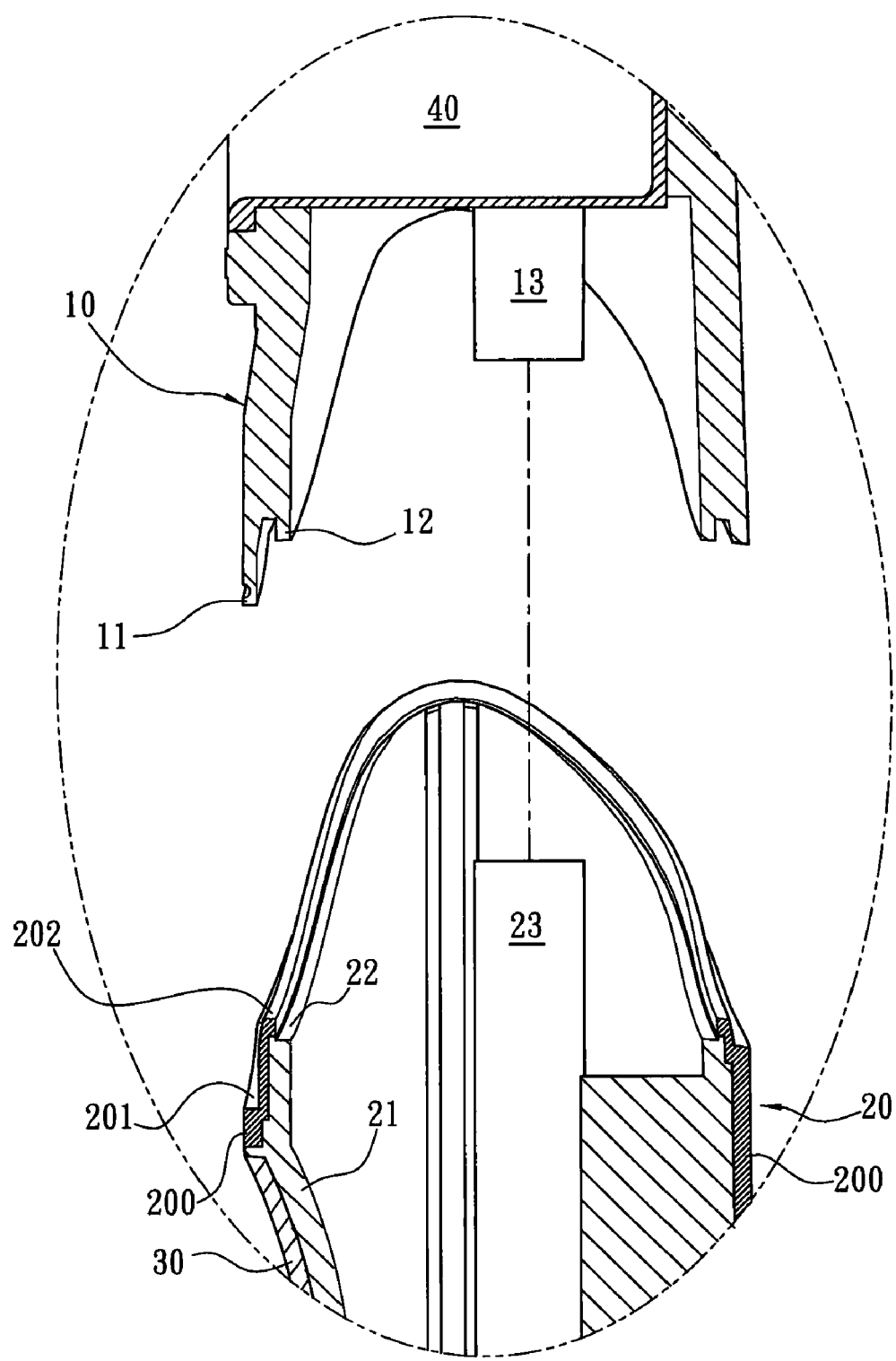
FIG. 3C is a fragmentary enlarged view according to FIG. 3B.
Figure 4:
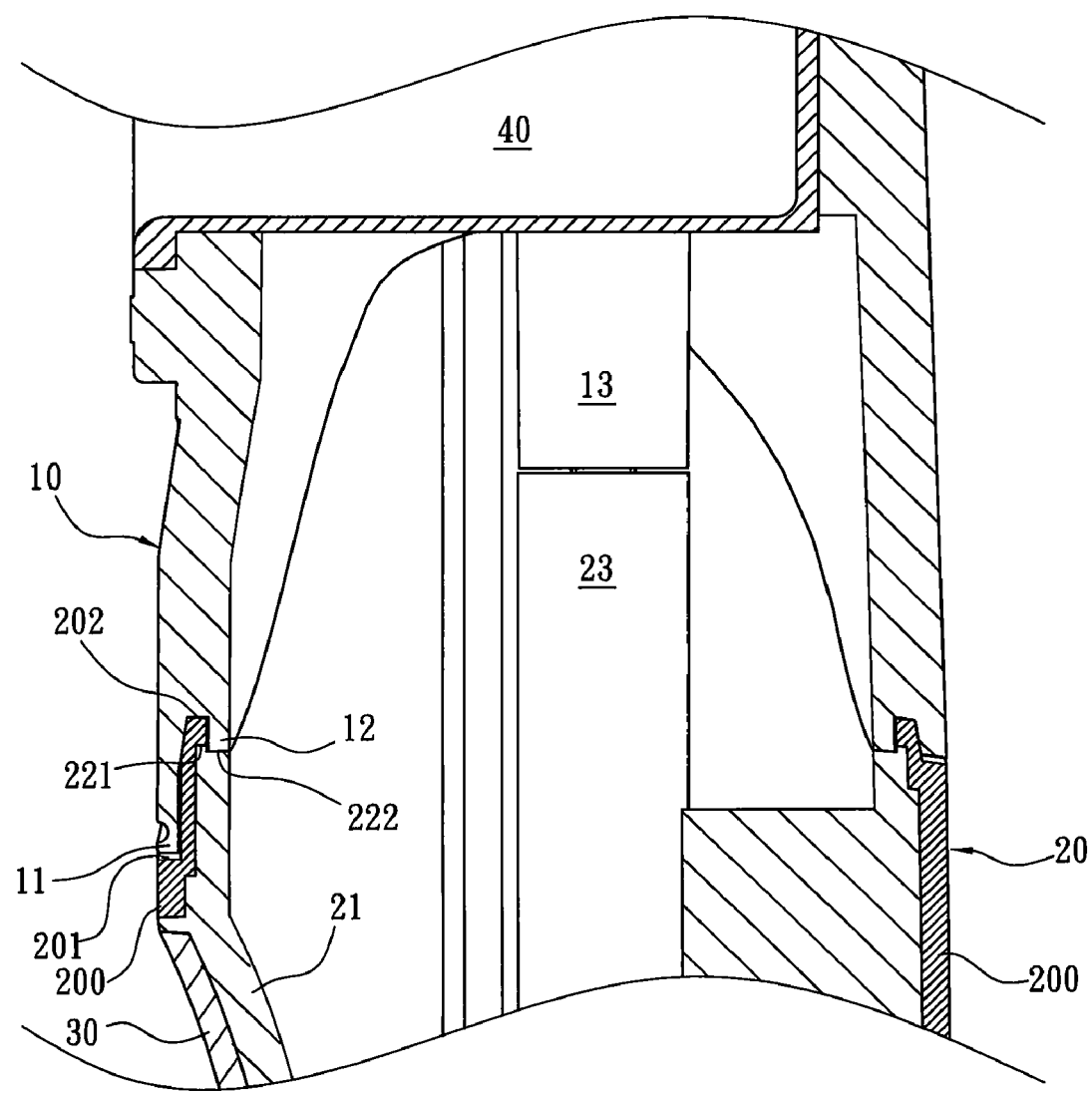
FIG. 4 is a schematic view according to FIG. 3C showing the hard upper casing and the lower casing in a coupled condition.

Please refer to FIGS. 1 through 4, the present invention aims to provide a waterproof housing structure for portable optical analyzer. The waterproof housing structure 1 mainly comprises a hard upper casing 10, a lower casing 20 and a fastening element 50. The hard upper casing 10 has an outer rim 11, an inner rim 12 and an indented liquid sample chamber 40 on the surface, and an upper fastening strut 13 extended inside. The lower casing 20 includes a hard inner shell 21 and a pliable cap 200. The hard inner shell 21 contains a trapezoidal rim 22 which has a first trapezoidal surface 221 on an outer side and a second trapezoidal surface 222 on an inner side lower than the first trapezoidal surface 221 to mate and couple with the inner rim 12 of the upper casing. The pliable cap 200 is made from thermo plastic elastomer to wrap a portion of outer surface of the hard inner shell 21, and has an outer edge 201 mating and coupling with the outer rim 11 of the upper casing, and an inner edge 202 mating with the interval of the outer rim 11 and inner rim 12 of the upper casing. The inner edge 202 has a portion located on the first trapezoidal surface 221. The lower casing 20 also has an extended lower fastening strut 23 corresponding to the upper fastening strut 13. The lower casing 20 further has a panel bonding zone 24 on the outer surface of the hard inner shell 21 to bond an operation panel 30. The operation panel 30 has a display zone 31. The waterproof housing structure 1 further has a battery lid 60 formed on the lower casing 20. The battery lid 60 has a waterproof washer 61 (such as a rubber pad) interposed between the battery lid 60 and the lower casing 20. The upper fastening strut 13 has a coupling hole 131 and the lower fastening strut 23 has a fastening hole 231. The fastening element 50 runs through the coupling hole 131 of the upper fastening strut 13 to engage with the fastening hole 231 of the lower fastening strut 23 to fasten the hard upper casing 10 to the lower casing 20. The fastening element 50 is coupled with a waterproof ring 51 (such as a rubber pad) interposed between the fastening element 50 and the upper fastening strut 13.

When in use, a liquid sample is held in the liquid sample chamber 40 of the upper casing 10 and can be directly accessed without permeating into the waterproof housing structure 1 through the seam between the hard upper casing 10 and the lower casing 20, thus usability improves. Moreover, by providing the pliable cap 200 wrapped by a portion of the outer surface of the hard inner shell 21 on the lower casing 20, the concern of liquid permeation that might incur to the coupled irregular rims of the hard upper casing 10 and lower casing 20 (including the outer rim 11, inner rim 12, trapezoidal rim 22, outer edge 201 and inner edge 202) can be averted. In addition, assembling the hard upper casing 10 and the lower casing 20 during production or repair and maintenance does not need to assembly extra waterproof elements (such as rubber pads). The outer edge 201 of the pliable cap 200 can be correspondingly coupled on the outer rim 11, and the inner edge 202 can mate the interval of the outer rim 11 and inner rim 12. Hence assembly of the hard upper casing 10 and the lower casing 20 can be accomplished easily. By partly wrapping the hard inner shell 21 with the pliable cap 200, a pliable surface is provided to smooth grasp and an anti-slipping effect also can be achieved. Thus it provides significant improvement over the conventional technique.

While the preferred embodiment of the invention has been set forth for the purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A waterproof housing structure for portable optical analyzer, comprising:
 a hard upper casing which includes an outer rim and an inner rim and an indented liquid sample chamber on the surface, and an upper fastening strut extended inside; and
 a lower casing which includes a hard inner shell and a pliable cap; the hard inner shell including a trapezoidal rim which contains a first trapezoidal surface on an outer side and a second trapezoidal surface on an inner side lower than the first trapezoidal surface to mate and couple with the inner rim; the pliable cap wrapping a portion of outer surface of the hard inner shell and containing an outer edge to couple with the outer rim and an inner edge to mate an interval between the outer rim and the inner rim, the inner edge being partly located on the first trapezoidal surface, the lower casing further including a lower fastening strut extended inside corresponding to the upper fastening strut; and
a fastening element running through the upper fastening strut to engage with the lower fastening strut to fasten the hard upper casing to the lower casing.

2. The waterproof housing structure for portable optical analyzer of claim 1, wherein the pliable cap is made from thermo plastic elastomer.

3. The waterproof housing structure for portable optical analyzer of claim 2, wherein the upper fastening strut includes a coupling hole to receive insertion of the fastening element and the lower fastening strut includes a fastening hole to engage with the fastening element to fasten the upper fastening strut to the lower fastening strut, the fastening element being coupled with a waterproof ring interposed between the fastening element and the upper fastening strut.

4. The waterproof housing structure for portable optical analyzer of claim 1, wherein the upper fastening strut includes a coupling hole to receive insertion of the fastening element and the lower fastening strut includes a fastening hole to engage with the fastening element to fasten the upper fastening strut to the lower fastening strut, the fastening element being coupled with a waterproof ring interposed between the fastening element and the upper fastening strut.

5. The waterproof housing structure for portable optical analyzer of claim 4 further comprising a battery lid located on the lower casing, the battery lid including a waterproof washer interposed between the battery lid and the lower casing.

6. The waterproof housing structure for portable optical analyzer of claim 3 further comprising a battery lid located on the lower casing, the battery lid including a waterproof washer interposed between the battery lid and the lower casing.

7. The waterproof housing structure for portable optical analyzer of claim 1 further comprising a battery lid located on the lower casing the battery lid including a waterproof washer interposed between the battery lid and the lower casing.

8. The waterproof housing structure for portable optical analyzer of claim 5, wherein the lower casing further comprises a panel bonding zone on the outer surface of the hard inner shell and the waterproof housing structure includes an operation panel bonding to the panel bonding zone, the operation panel including a display zone.

9. The waterproof housing structure for portable optical analyzer of claim 3, wherein the lower casing further comprises a panel bonding zone on the outer surface of the hard inner shell and the waterproof housing structure includes an operation panel bonding to the panel bonding zone, the operation panel including a display zone.

10. The waterproof housing structure for portable optical analyzer of claim 1, wherein the lower casing further comprises a panel bonding zone on the outer surface of the hard inner shell and the waterproof housing structure includes an operation panel bonding to the panel bonding zone, the operation panel including a display zone.

* * * * *